United States Patent [19]

Portier

[11] Patent Number: 4,775,650

[45] Date of Patent: Oct. 4, 1988

[54] DECONTAMINATION OF CONTAMINATED STREAMS

[75] Inventor: Ralph J. Portier, Baton Rouge, La.

[73] Assignee: Louisana State University, Baton Rouge, La.

[21] Appl. No.: 3,019

[22] Filed: Jan. 13, 1987

Related U.S. Application Data

[63] Continuation-in-part of Ser. No. 918,840, Oct. 14, 1986.

[51] Int. Cl.$^4$ .............................................. B01J 20/22
[52] U.S. Cl. ..................................... 502/62; 502/402;
502/404; 502/527; 210/688; 210/691
[58] Field of Search .................. 502/402, 404, 527, 62

[56] References Cited

U.S. PATENT DOCUMENTS 4,356,236  10/1982  Koshugi ......................... 502/404 X

FOREIGN PATENT DOCUMENTS 152685  12/1979  Japan ................................. 502/404
167043  12/1980  Japan ................................. 502/404
1268352 11/1986  Japan ................................. 502/404

Primary Examiner—Patrick P. Garvin
Attorney, Agent, or Firm—Llewellyn A. Proctor

[57] ABSTRACT

This disclosure relates to compositions characterized as porous solids on the surfaces of which thin films of chitinous material are dispersed, and to a process employing chitin per se, and preferably the chitin coated compositions, supra, as contact masses for the removal of metals contaminants, or halogenated organic compounds, from liquid streams contaminated or polluted with these materials.

7 Claims, No Drawings

DECONTAMINATION OF CONTAMINATED STREAMS

REFERENCE TO OTHER APPLICATIONS

This is a continuation-in-part of Application Ser. No. 918,840, filed Oct. 14, 1986 (pending), herewith incorporated and made of reference.

FIELD OF THE INVENTION

This invention relates to a composition useful for the decontamination or detoxification, of contaminated or toxin-polluted streams, and to a process for the decontamination or detoxification of contaminated or toxin-polluted streams utilizing said compositions.

BACKGROUND AND PROBLEMS

The use of a wide variety of toxic chemicals in agriculture has presented recognizable problems, as well as potential hazards in terms of land use, and extant danger to wetland systems. Moreover, an array of toxic chemicals are discharged from diverse industrial facilities, these including accidental spills and the creation of dump areas which form a continuing source of pollution. These discharges, spills and dump sites create direct hazards to the use of land, and have caused serious drinking water contamination, and other health problems. Often these chemicals find their way into wetlands systems. For example, the coastal zone of Louisiana contains an ecosystem of more than seven million acres of marshes and estuaries representing approximately 40 percent of the total coastal wetland area of the lower forty-eight states of the United States. The gulfward movement of water introduces a wide variety of organic materials, including potentially hazard chemicals, into highly productive shrimp nursery grounds. The widespread use over the last several decades of herbicides, pesticides, and other chemicals in this geographical area has raised serious questions concerning the effect of these chemicals on the environment. Such toxic agents include e.g., organochlorides, polychlorobiphenyls (PCB's) and chlorinated phenols all of which have been noted for their recalcitrant nature as regards elimination of these contaminants from the environment.

Large volumes of process waters, containing a changing organic chemical matrix of these and other toxic contaminants, are discharged by industrial plants located in this area following biological oxidation in aerated lagoons and/or activated sludge systems. Such aerobic systems have the ability to reduce the total BOD and COD of the effluents but are subject to upsets due to shifting effluent load from one toxicant class to another. It has been deemed advantageous to apply enzymes to the treatment of these systems since enzymes are biocatalytic materials which possess extraordinary high efficiency, have specific properties, and can be used to catalyze almost any chemical reaction, without producing harmful substances. The use of enzymes, and microorganisms to biotransform and biodegrade these materials into harmless substances, however, has met with limited success largely because of the difficulty in accomplishing such objective within an acceptable time frame.

Solutions of metal salts are another class of by-product of industrial facilities which presents an environmental clean-up problem; or the problem may be born of a need, or desire, to economically recover the metals values. Silver salts, e.g., silver chloride, a metal or salt of considerable value, is thus found in the waste streams of certain industrial processes, for which reason per se its recovery is highly desirable. Other contaminant metals, e.g., such heavy metals as lead, mercury and arsenic, are hazardous per se and may present a health hazard if not removed from the by-product streams of industrial plants prior to discharge to the environment. Yet other contaminant metals may raise both a health hazard, and an economic loss due to the potential value of the metals, e.g., zinc, chromium, cadmium and nickel.

OBJECTS

Accordingly, it is the primary objective of the present invention to overcome these and other prior art disadvantages by providing a composition useful for the decontamination, or detoxification, of contaminated or toxin-polluted streams, and process for the passage of a contaminant-containing or toxin-polluted stream through a bed of said composition to decontaminate or detoxify said stream.

A specific object is to provide novel compositions suitable for use in the continuous decontamination, or detoxification of contaminated, or toxic chemical-containing streams brought into contact therewith at high detoxification rates.

A further object is to provide a process utilizing these compositions, and others, for the decontamination or detoxification of metals-containing, or toxic chemical-containing streams contacted therewith.

THE INVENTION

These objects and others are achieved in accordance with the present invention embodying:

(i) a composition characterized as a porous solid on the surface of which chitin or chitosan, an aminopolysaccharide, is dispersed as a thin film, and (ii) a process utilizing a bed of chitin, or chitosan, per se or preferably the composition of (i) for the contact therewith of a stream which contains a metal, or metal salts, or compounds for the removal of said metal, or metal salts, or compounds and consequent decontamination of said stream, or stream which contains a toxic halogenated organic compound, or compounds, for the removal of said halogenated organic compound, or compounds, and detoxification of said stream, or both.

It has been found that a chitinous material per se as found in nature, or a composition formed by dispersing said chitinous material, or aminopolysaccharide, as a surface layer, film, or coating upon a porous solids substrate, preferably a particulate solids substrate, can be used to remove a metal salt, metal salts, or compounds from liquid streams within which the salt, salts, or compounds, is dissolved, or to remove a halogenated organic compound, or compounds, from liquid streams which contain such compound, or compounds, as a toxic impurity. Chitin, chitosan or n-carboxy chitosan, e.g., chitin as a waste product derived from the chitinous exoskeleton of shellfish, such as the fresh water crayfish (*Procambarus clarkii*), shrimp, crabs and the like, can thus be particulated, or shreaded into small pieces and directly employed as a contact mass for the removal from said liquid streams of said metal, metal salts, or compounds (hereinafter metal salt, or salts) or halogenated organic compound, or compounds. Preferably however, the chitinous material is solubilized and then dispersed upon a mass of porous particulate solids in the form of spheres, beads, extrudates and the like to form a surface layer, film, or coating, this material being particularly efficient as a contact mass for effecting the removal of a metal, or metal salts, or a halogenated organic compound, or compounds, from a liquid stream containing either or both of these materials.

Solid surfaces to which the aminopolysaccharide, e.g., chitin, chitosan, n-carboxy chitosan or the like, can be affixed are quite large, and include numerous porous inorganic oxides exemplary of which are, e.g., (1) silica or silica gel, clays, and silicates including those synthetically prepared and naturally occurring, which may or may not be acid treated, for example, attapulgus clay, china clay, diatomaceous earth, fuller's earth, kaolin, kieselguhr, etc.; (2) ceramics, porcelain, crushed firebrick, bauxite; (3) synthetic and naturally occurring refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, silica carbide, boron nitride, etc.; (4) crystalline zeolitic aluminosilicates such as naturally occurring or synthetically prepared mordenite and/or faujasite, either in the hydrogen form or in a form which has been treated the multavalent cations; (5) spinels such as $MgAl_2O_4$, $FeAl_2O_4$, $ZnAl_2O_4$, $MnAl_2O_4$, $CaAl_2O_4$ and other like compounds having the formula $MO.Al_2O_3$ where M is a metal having a valence of 2; and (6) combinations of elements from one or more of these groups.

The solid support surface to which the chitinous material, or aminopolysaccharides, can be affixed to form compositions which can be used advantageously as a contact mass for practicing the process of this invention can be in virtually any configuration, shape, or size which exposes the chitinous mass disposed thereon to the stream to be treated. The choice of configuration, shape, and size of the refractory inorganic oxide depends on the particular circumstances of use of the method of this invention. Generally, in operations wherein the compositions are disposed as a fixed bed in an immobile vessel, the support surface can be conveniently employed in particulate form, as pills, pellets, granules, rings, spheres, rods, hollow tubes, and the like. Exemplary of preferred materials of hollow tubular shape are, e.g., Amicon's ultrafiltration membranes cast from a variety of polymer solutions, these consisting of membrances of a very thin (0.1 to 1.5 mm), dense "skin" of extremely fine, controlled pore structure which opens to a much thicker (50 to 250 mm), open-celled spongy layer of the same polymer, e.g., poly-sulfone or acrylic copolymers. The tubes can be of virtually any length, with the diameters of such tubular specimens ranging generally from about 30 cm to about 300 cm, preferably from about 75 cm to about 125 cm. The chitinous coated compositions formed on such substrates can be employed as fixed beds or moving beds, generally the former. The chitinous coated particles are sized in accordance with accepted engineering principles to provide good contact between the contaminated or toxin-containing liquid stream and the particles.

The aminopolysaccharide chitin, a polymer of N-acetyl-d-glucosamine, is found in abundance in aquatic ecosystems, and techniques for solubilizing chitin and chitin derivitives per se are well known. The exoskeleten of crayfish, shrimp or crabs, e.g., can be particulated, cleaned, and solubilized, or dissolved in a mineral acid or organic acid solution, suitably the latter, or in an organic solvent. For example, the exoskeleton of the shellfish can be dissolved in an aqueous solution of an organic acid exemplary of which is formic acid, acetic acid, butyric acid, capric acid, propiolic acid, cyclobutanecarboxylic acid, trimellitic acid and the like. The chitin or chitinous material is solubilized at ambient conditions or by warming at pH ranging from about 2 to about 6, preferably about 3 to about 5. Organic solvents, e.g., aldehydes, ketones, and the like are also useful for solubilizing the chitin. Exemplary of the aldehydes are those characterized by the formula RC(O)H wherein R is H, alkyl, alkenyl, alkynyl, aryl, alkaryl, arylalkyl, or the like, e.g., acetaldehyde, butyaldehyde, heptaldehyde, phenylacetaldehyde, o-tolualdehyde, p-hydroxybenzaldehyde; whether saturated or unsaturated, e.g., crotonaldehyde; and including dialdehydes, e.g., glutaraldehyde; trialdehydes, e.g., 4-formylbutanoic acid, cyclopentanecarbaldehyde and the like. Exemplary ketones are those characterized by the formula $R-R(O)R^1$ wherein R and $R^1$ can be the same or different, and selected from H, alkyl, alkenyl, alkynyl, aryl, alkaryl, arylalkyl groups and the like, e.g., acetone, ethyl propyl ketone, methyl isopropyl ketone, methyl heptyl ketone, methyl vinyl ketone; and ketenes such as dimethylketene, diphenylketene and the like. The chitin or chitosan is digested within the organic solvent via chemical modification of the beta linkages of the chitin. Compositions particularly useful for the removal of a metal, metal salts or compounds from a stream contaminated therewith, or the detoxification of a stream containing a halogenated organic compound, or compounds, by contact of said stream therewith, are formed by contacting a solution of the solubilized chitin and a particulate porous solid therewith, suitably by immersion of the particulate chitinous solids within the solution, next separating the wetted solids from the solution as by decantation or filtering and then drying the solids to remove the liquid portion of the solution to produce deposition of the chitin upon the solids substrate. Suitably, the wet solids are dried at temperatures ranging above about 25° C., or at higher temperatures insufficient to decompose the chitin. Preferably, the drying step is conducted at temperatures ranging from about 50° C. to about 75° C. for periods ranging from about 1 hour to about 24 hours, preferably from about 3 hours to about 6 hours. Drying can be conducted at ambient conditions or under vacuum.

In coating the solids particles, the concentration of the chitin in the solution is adjusted to give a film of the desired thickness. Generally the concentration of the solution is adjusted to provide a continuous or discontinuous film ranging in thickness from about 10 microns to about 200 microns, preferably from about 25 microns to about 100 microns. Films, or coatings, within these ranges of thickness provide particles containing generally from about 0.5 percent to about 1.5 percent total carbon, based on the total weight of the chitinous film. Whereas films of greater thickness can be used, they generally provide no particular advantage and indeed can impede the effectiveness of the separation. The viscosity of the solutions used to form the chitinous coatings on solids substrates generally ranges from about 75 CPS to about 500 CPS. Preferably, those employed for use in metal salts removal ranges from about 75 CPS to about 200 CPS, and those for removal of halogenated organic compounds from about 300 CPS to about 500 CPS. Solutions of such viscosity range generally contain from about 0.75 percent to about 2 percent, or from about 0.5 percent to about 1.5 percent chitin, respectively, based on the weight of the solution.

A bed of chitin-coated composition, or bed formed from chitin or chitosan directly obtained via the treatment of waste from a shellfish processing plant, on contact at acidic or near-acidic conditions, with a liquid stream contaminated or polluted with a metal, or metal salts, or halogenated organic compound, or compounds, or both, which effectively remove the contaminant or pollutant from the liquid stream. On contact of the contaminated or polluted stream, preferably at pH ranging from about 3 to about 8.5, more preferably at pH of from about 4 to about 6, with the chitinous contact mass the contaminant or pollutant will adhere to the chitinous solid substrate, and the effluent passed through the bed will contain less or none of the contaminant or pollutant. One or a series of beds of the chitinous contact mass can be employed, the beds can be employed in series or in parallel, or the beds can be employed both in series and in parallel, and the contacting steps can be staged in accordance with accepted engineering principles to remove substantially all of the contaminant, or pollutant, from a contaminated or polluted liquid stream.

The metal salt, or salts, and the halogenated organic compound, or compounds, complex with the chitinous solids contact mass, adhering to the chitinous solids contact mass by adsorption, absorption or other mechanism. Whereas there is no desire to be bound by any specific theory of mechanism, it is believed that the metal salt, or metal salts, form a chelate with the chitinous solids contact mass. The halogenated organic compounds are, on the other hand, believed to complex with the chitinous solids via a covalent bonding mechanism between the halogen and the chitin. A feature of the invention in any event, is that the metal, or metal salts, or the halogenated organic compound, or compounds, if desired, can be readily recovered from the chitin-complex by contacting the chitin-complex in an additional step with an alkaline solution sufficient to chemically alter the chitin and decompose the chitin-complex, suitably by use of a solution of pH ranging above about 8, preferably at pH ranging from about 8 to about 11. The chitin-complex can be contacted with the alkaline solution at ambient conditions, or at elevated temperatures, suitably at temperatures above about 50° C., preferably from about 50° C. to about 100° C. The reaction with the chitin-complex is believed to involve a chemical attack upon the B-linkages which tend to unravel, and break down the chitin. Once the chitin-metals complex is broken, or dissolved, in any event, the metals can be recovered from the solution by various processes known in the art; these methods per se forming no part of the present invention. The complex of the chitin-halogenated organic compound can be treated in similar manner to detoxify same. The chitin-halogenated organic compound complex is considered primarily as a hazardous waste, and hence it is generally detoxified in this manner and made safe for return to the environment; but may be used as a source of raw materials for reprocessing.

A wide class of metals, metal salts, or compounds thereof can be recovered from waste streams in accordance with this invention. Exemplary of the metals per se which can be recovered thereby are the alkali or alkaline-earth metals, or both, e.g., sodium, calcium, magnesium, etc.; the Group IB metals (Periodic Table of the Elements; Sargent-Welch Scientific Company, Copyright 1968), e.g., copper, silver and gold; the the Group IIB metals, e.g., zinc; the Group III metals, or metaloids, e.g., aluminum; the Group IV metals, e.g., lead; the Group V metals, e.g., arsenic; the Group VI metals, e.g., chromium; the Group VII metals, e.g., manganese; and the Group VIII metals, e.g., iron, nickel and the like. The metals can exist in virtually any form in aqueous or non-aqueous solution, e.g., as a halide, sulfate, sulfite, nitrate, nitrite, phosphate, formate, acetate, or the like.

Exemplary of the halogenated organo compounds which can be removed from solution in accordance with the practice of this invention are halogenated phenols, e.g., 2-chlorophenol, pentachlorophenol (PCP), pentabromophenol (PBP), polychlorobiphenyls (PCB's), benzenehexachloride (BHC), chlorinated ethane, ethyl bromide, vinyl chloride, and the like.

The invention, and its principle of operation will be more fully understood by reference to the following examples presenting data illustrating its more salient features. All parts are given in terms of weight except as otherwise expressed.

EXAMPLES 1–4

In obtaining these data, chitosan was coated upon a diatomaceous earth substrate, the chitosan having been derived from the fresh water crayfish *Procambarus clarkii* by removal of the chitinous exoskeleton. The chitinous exoskeleton was dried at 60° C. for 24 hours, then solubilized and dispersed on particles of diatomaceous earth. The diatomaceous earth is a calcined SiO$_2$/Clay mixture marketed by Manville Sales Corporation under the tradename "CELLITE", and the crystalline silica content ranges up to 10 wt. percent. The particles of diatomaceous earth were immersed at ambient temperature in a chitinous solution of 300 CPS viscosity, separated by decantation from the solution after 1.0 hour, and then dried in air at at 60° C. over a period of 24 hours. The particles, found to contain a chitinous film of 100 microns average thickness, and containing from about 0.5 percent to 1.5 percent chitosan by dry weight for each bead (based on total carbon analysis), were charged as a packed bed to a tubular glass reactor provided with means for the introduction of an influent, and for the removal of an effluent. Influent liquid streams with metals salts dissolved therein, in differing concentrations, at pH=7.8 were then introduced upflow and downflow into the reactor. The specimens were acid digested and analyzed by inductively coupled plasma. Duplicate samples showed no significant difference in results. The results are discussed below.

Referring specifically to Table 1, the first column identifies each of the cationic metals contained within the streams made up for use in the four separate tests, viz. As, Cr, Ni and Zn. During each of the four runs the metals concentrations were increased, or amended from a low point to a high point, the minimum and maximum concentrations in mg/l being specifically identified by reference to the second and third columns of the table. Thus, two solutions of each metal were tested: low metal amendments contained 6–15 mg/l analyte, and high metal amendments contained 50–271 mg/l analyte. The fourth column of the table shows the actual concentration of each of the metals in the respective effluent stream, both at the time of, and after increasing the metals concentration within the influent stream. The last, or fifth column of the table shows the percent metal removed, both prior to and after amendment to increase the metals concentration.

A second pass of a metals-containing stream through the column did not significantly enhance metal removal.

Unspiked controls were passed through the column. A 2–3x increase in metal levels were noted for Zn (0.42 to 0.87 mg/l), Ni (0.75 to 2.86 mg/l) and As (0.1 to 0.3 mg/l). Adjusting for these elevated effluents, Ni removals approached 100%, Zn removals approached 98%, and As removals approached 99%.

TABLE 1

UNOPTIMIZED METAL REMOVALS BY CHITIN COATED SOLIDS TREATMENT IN A FIXED BED REACTOR

| METAL | AMEND-MENT | METAL CONCENTRATION (MG/L) INITIAL | POST-TREATMENT | % REMOVAL |
|---|---|---|---|---|
| As | low | 10.4 | 0.4 | 96 |
|    | high | 271.0 | 1.3 | 99 |
| Cr | low | 6.3 | 0.38 | 94 |
|    | high | 51.5 | 0.75 | 99 |
| Ni | low | 10.0 | 2.6 | 74 |
|    | high | 77.7 | 2.7 | 97 |
| Zn | low | 13.7 | 0.95 | 93 |
|    | high | 111 | 3.5 | 97 |

The following data shows that metals can also be effectively removed from an influent metals-containing stream in a slurry bed reactor.

EXAMPLES 5–8

Chitin coated solids as employed in preceding Examples 1–4 were powdered, slurried in an aqueous medium to provide a 20 wt.% solids slurry, the slurry charged into a top inlet at one end of a horizontal reactor, and continously agitated while spent slurry was removed via a bottom inlet from the opposite end of the ractor. A metals-containing influent stream was introduced via an inlet adjacent the slurry inlet side of the reactor, and an effluent stream removed via an outlet adjacent the slurry outlet side of the reactor. The identity of each of the metals (Cr, Ni, Zn) within the influent stream, the concentration of each of the metals, respectively, within the influent stream, and the concentration of each of the metals within the effluent stream after treatment over the chitin coated solids, respectively, and the unoptimized percent metal removal are given in Table 2.

TABLE 2

UNOPTIMIZED METAL REMOVALS BY CHITIN COATED SOLIDS TREATMENT IN A SLURRY REACTOR

| METAL | METAL CONCENTRATION (MG/L) INITIAL | POSTTREATMENT | % REMOVAL |
|---|---|---|---|
| Cr | 9.86 | 0.53 | 94.6 |
| Ni | 10.73 | 1.89 | 82.4 |
| Zn | 13.40 | 0.61 | 95.4 |

EXAMPLE 9

A run was made employing a fixed bed reactor, and chitin coated solids as in Examples 1–4, except that in this instance a mine leachate stream of pH ranging from 2.3 to 2.8 containing a wide spectrum of metals was introduced to the reactor. The effluent was analyzed as in Examples 1–4.

Table 3 shows the identity of each of the metals found in the acid leachate stream, and the concentration in parts per million (ppm) of each of the metals in the influent stream (Column 2) and the effluent stream (Column 3), respectively.

TABLE 3

TREATMENT OF AN ACID LEACHATE STREAM

| METALS | METALS CONCENTRATION OF INFLUENT (ppm) | METALS CONCENTRATION OF EFFLUENT (ppm) |
|---|---|---|
| As | 190 | <10 |
| Fe | 6000 | 30 |
| Pb | <1 | <1 |
| Cu | 9 | <1 |
| Al | 110 | <10 |
| Ca | 550 | 60 |
| Mg | 3200 | 70 |

EXAMPLE 10

A run in accordance with Examples 1–4 was again repeated except that in this instance the influent stream to the reactor, packed with the chitin coated solids, was water to which was added Aroclors ™ 1232, 1248 and 1254, i.e., a commercial mixture of polychlorinated-biphenyls (PCB's), containing in large part 4,4$^1$-dichlorobiphenyl (4;4$^1$-DCB), 2,5,4$^1$-trichlorobiphenyl (2,5,4$^1$ TCB) and 2,4,5,2$^1$,5$^1$-pentachlorobiphenyl (2,4,5,2$^1$,5$^1$ PCB). The initial concentration of each in the influent is 5 ppm as given in Table 4. After passage of the toxic effluent at pH=6.4 through the bed of chitinous coated solids, the solids were collected by means of filtration, extracted with a hexane/methylene chloride (85%/15%) solvent to recover the PCB cogeners and Aroclor ™ and the solvent then subjected to gas chromatographic analysis to determine the recovery. This is given in the third column of Table 4, and calculated percent recovery is given in the fourth column of Table 4.

TABLE 4

GAS CHROMATOGRAPHIC RECOVERY OF PCB COGENORS AND AROCLOR ™ MIXTURES ON CHITIN COATED SOLIDS

| TOXICANT | INITIAL CONCENTRATION ppm | FINAL CONCENTRATION | % RECOVERY |
|---|---|---|---|
| 4,4$^1$ DCB | 5 | 4.61 +/− 0.2 | 92.2 |
| 2,5,4$^1$ TCB | 5 | 4.78 +/− 1.7 | 95.6 |
| 2,4,5,2$^1$,5$^1$-PCB | 5 | 4.66 +/− 0.31 | 93.2 |
| Aroclor 1232 | 5 | 4.18 +/− 0.26 | 83.6 |
| Aroclor 1248 | 5 | 4.23 +/− 0.41 | 84.6 |
| Aroclor 1254 | 5 | 4.38 +/− 0.16 | 87.6 |

It is apparent that various modifications can be made as will be known to those skilled in this art, without departing the spirit and scope of the invention.

Having described the invention, what is claimed is:

1. A composition useful for the decontamination and removal of a metal from a metal-contaminated liquid stream, or the detoxification and removal of a toxic halogenated organic compound from a liquid stream containing said toxic compound, by the contact therewith of said contaminated or toxin polluted liquid stream which comprises: a porous solid on the surface of which chitin is dispersed as a film of thickness sufficient to complex with and remove metal from said metal-contaminated liquid stream, or toxic halogenated organic compound from said toxin polluted liquid stream.

2. The composition of claim 1 wherein the chitinous film ranges in thickness from about 10 microns to about 200 microns.

3. The composition of claim 2 wherein the chitinous film is of thickness ranging from about 25 microns to about 100 microns.

4. The composition of claim 1 wherein the chitinous film ranges in thickness from about 10 microns to about 200 microns, contains from about 0.5 percent to about 1.5 percent total carbon by weight, the solid substrate on which the chitinous film is dispersed is a particulate porous inorganic oxide or a polymeric membrane cast from a polymeric solution, and the solid substrate is in the form of pills, pellets, granules, rings, spheres, rods, or hollow tubes.

5. The composition of claim 4 wherein the solid substrate on which the chitinous film is dispersed is a polymeric membrane cast from a polymeric solution, and is of tubular shape.

6. The composition of claim 1 wherein the chitinous film ranges in thickness from about 10 microns to about 200 microns, and the particulate porous solids substrate is selected from the groups consisting of (1) silica, silica gel, clays, and silicates; (2) ceramics, porcelain, crushed firebrick, bauxite; (3) alumina, titanium dioxide, zirconium dioxide, chromium oxide, zinc oxide, magnesia, thoria, boria, silica-alumina, silica-magnesia, chromia-alumina, alumina-boria, silica-zirconia, silica carbide, and boron nitride; (4) crystalline zeolitic aluminosilicates; (5) spinels; and (6) combinations of elements from one or more of these groups.

7. The composition of claim 6 wherein the chitinous film ranges in thickness from about 25 microns to about 100 microns.

* * * * *